(12) United States Patent
Yukov

(10) Patent No.: US 11,083,432 B2
(45) Date of Patent: Aug. 10, 2021

(54) YUKOV TISSUE CHARACTERIZATION METHOD AND APPARATUS

(71) Applicant: Igor Yukov, Orange, CT (US)

(72) Inventor: Igor Yukov, Orange, CT (US)

(*) Notice: Subject to any disclaimer, the term of this patent is extended or adjusted under 35 U.S.C. 154(b) by 0 days.

(21) Appl. No.: 16/676,480

(22) Filed: Nov. 7, 2019

(65) Prior Publication Data

US 2020/0077978 A1 Mar. 12, 2020

Related U.S. Application Data

(60) Continuation of application No. 16/504,276, filed on Jul. 7, 2019, now Pat. No. 10,687,787, which is a division of application No. 15/732,780, filed on Dec. 29, 2017, now Pat. No. 10,383,597, which is a continuation-in-part of application No. 14/998,914, filed on Mar. 4, 2016, now abandoned.

(51) Int. Cl.
*A61B 8/14* (2006.01)
*A61B 8/08* (2006.01)
*A61B 8/00* (2006.01)

(52) U.S. Cl.
CPC .............. *A61B 8/145* (2013.01); *A61B 8/08* (2013.01); *A61B 8/4416* (2013.01); *A61B 8/5223* (2013.01); *A61B 8/5246* (2013.01); *A61B 8/4488* (2013.01); *A61B 8/463* (2013.01); *A61B 8/469* (2013.01); *A61B 8/5269* (2013.01); *A61B 8/56* (2013.01)

(58) Field of Classification Search
CPC .......... A61B 8/463; A61B 8/145; A61B 8/08; A61B 8/4488; A61B 8/4494; A61B 8/5246

USPC .......................................................... 600/447
See application file for complete search history.

(56) References Cited

U.S. PATENT DOCUMENTS

| 3,881,164 A | 4/1975 | Kossoff | |
|---|---|---|---|
| 4,932,414 A | 6/1990 | Coleman | |
| 5,361,767 A * | 11/1994 | Yukov | A61B 8/0858 600/442 |
| 5,617,866 A * | 4/1997 | Marian, Jr. | A61B 8/00 600/459 |

(Continued)

FOREIGN PATENT DOCUMENTS

| CN | 1249164 | 4/2000 |
|---|---|---|
| CN | 1113631 C | 7/2003 |

(Continued)

OTHER PUBLICATIONS

Aldrich, "Basic physical of ultrasound imaging", 2007, Crit Care Med 2007 vol. 35 Suppl., No. 5, S131-S137 (Year: 2007).*

*Primary Examiner* — William V Gilbert
(74) *Attorney, Agent, or Firm* — Ingenium Patents LLC; Peter R. Kramer

(57) ABSTRACT

A systems and methods for tissue characterization using ultrasound are disclosed. One embodiment is for a system with a novel YB-scan transducer. The YB transducer is comprised of a plurality of separate and independent piezo-elements. The system is configured to scan a tissue or organ using two different frequencies to produce 2D images and two-frequency attenuation data to characterize tissue types. Other embodiments are presented permitting conventional B-scan imaging combined with A-mode scanning for two-frequency tissue characterization.

6 Claims, 6 Drawing Sheets

(56) References Cited

U.S. PATENT DOCUMENTS

| | | |
|---|---|---|
| 6,007,489 A | 12/1999 | Yost et al. |
| 7,698,142 B2 | 4/2010 | Washburn |
| 2009/0005684 A1 | 1/2009 | Christopherson |
| 2009/0069686 A1* | 3/2009 | Daft ............... B06B 1/0292 600/459 |
| 2014/0163369 A1 | 6/2014 | Anuja |
| 2014/0350403 A1 | 11/2014 | Kho |
| 2015/0141822 A1 | 5/2015 | Miyauchi |
| 2017/0119352 A1* | 5/2017 | Anand ............... A61B 8/463 |

FOREIGN PATENT DOCUMENTS

| | | |
|---|---|---|
| WO | WO-2014113442 A1 | 7/2014 |
| WO | WO-2014186899 A1 | 11/2014 |
| WO | WO-2015104607 A1 | 7/2015 |

\* cited by examiner

YUKOV TISSUE CHARACTERIZATION METHOD AND APPARATUS

CROSS-REFERENCE TO RELATED APPLICATIONS

This application is a Continuation of pending application Ser. No. 16/504,276, filed on Jul. 7, 2019. Application Ser. No. 16/504,276 is a Division of Ser. No. 15/732,780 filed 2017 Dec. 29 that was issued as U.S. Pat. No. 10,383,597 B2 on Aug. 20, 2019. Application Ser. No. 15/732,780 was a Continuation-In-Part of application Ser. No. 14/998,914 filed 2016 Mar. 4. This application claims benefit to the filing dates of application Ser. No. 16/504,276, application Ser. No. 15/732,780 and application Ser. No. 14/998,914. The contents of application Ser. Nos. 16/504,276, 15/732, 780 and 14/998,914 are, in their entirety, incorporated herein by reference.

BACKGROUND OF THE INVENTION

Field of the Invention

The present invention relates to systems and methods for non-invasively determining the type of tissue matter or the state of tissue matter in a living body. The present invention allows physicians and diagnosticians to determine the presence of healthy or unhealthy tissue and to determine a proper course of treatment.

Description of Related Art Including Information Disclosed Under 37 CFR 1.97 and 1.98

The present invention relates to improvement of the quality of existing ultrasound diagnostic examination by applying a combined transducer which can integrate a two-dimensional (YB-scan and B-scan) visualization technique with an A-mode transducer of a Two-Frequency Attenuation technique to obtain high quality ultrasound diagnostic examination including non-invasively determination the type of the issue matter under ultrasound investigation.

For many years specialists in ultrasound diagnostic field trying to develop an ultrasound diagnostic method and apparatus which can provide information to differentiate type of tissue through measuring attenuation data in a living body or by finding a pattern of the tissue type images. There are many attempts to reach that goal by using spectrum analyzes of reflected signals like U.S. Pat. No. 6,007,489 to Yost et al., European Patent No. 11840135 to Hironaka and many others that could not come up with an objective and reliable method for clinical applications. Some specialists like European Patent No. PCT/IB2014/067105 to Schneider, European Pat. No. PCT/CA2014/2014/050480 to Sadeghi, U.S. patent Ser. No. 14/096,960 to Anuja, European Pat. No. PCT/US2014/011631 to Chen and others tried to find a pattern in a tissue images to differentiate the type of tissue. All attempts to find some positive information to improve B-scan visualization examination to differentiate type of tissue was not successful since the amplitudes of reflected echo-signals depend not only on attenuation information from inside of the tissue structure but also on interference phenomena during reflection from the reflected surface, the angle of incident of the ultrasound pulses to reflected surface, its geometry and roughness. Attempts to find a system employing ultrasound methods for determination the nature of tissue within a living body is still continuing. One such system is disclosed in U.S. Pat. No. 5,361,767 to Yukov. This system determines a type of tissue by using methods and apparatuses for a "Two-Frequency Method" of tissue characterization which is based on applying two different frequencies and by registering reflected signals to calculate a differential attenuation coefficient of the tissue through formula I:

$$a(f_2) - a(f_1) = \frac{\frac{A_1(f_2)}{A_2(f_2)} - \frac{A_1(f_1)}{A_2(f_1)}}{2I} \text{db/Cm/MHz} \quad (I)$$

where $a(f_1)$ and $a(f_2)$—attenuation coefficient on frequencies $f_1$ and $f_2$ accordingly; $A_1(f_1)$, $A_2(f_1)$ and $A_1(f_2)$, $A_2(f_2)$ are amplitudes of the reflected signals from front and rare boundaries of a layer on frequencies $f_1$ and $f_2$ accordingly; I—is a thickness of a layer.

Author describes requirements for the reflected signals to be processed through mathematical algorithm since as mentioned there is no direct dependency between the amplitude of reflected signals and attenuation information. For that purpose, author suggests obtaining objective information related to attenuation data through analyses of the shape, width and registered time of reflected signals on applied two different frequencies. Chinese Patent No. CN1113631C to Korotkoff discloses a two-frequency method and apparatus which is based on a developed "Two-Frequency Method" described in U.S. Pat. No. 5,361,767. Author suggests using a conventional B-scan transducer with subtraction of the amplitudes of reflected signals automatically on two different frequencies and displaying the results as a two-dimensional attenuation image on the screen. As mentioned since there is no direct dependency between amplitudes of reflected signals and attenuation information the apparatus in Chinese Pat. No. CN1113631C for automatic two-dimensional attenuation image display cannot obtain objective attenuation information and it will be impossible to apply in the clinical environment as an objective diagnostic method. The U.S. Pat. No. 1,249,164 to Ke Jian with a Title "Human Tissue Ultrasonic Attenuation Imaging Technology" also applies a regular multi piezo elements B-scan transducer on two different frequencies and suggesting to apply separately two different regular_B-scan transducers on different frequencies "duplex frequency and double probe" which cannot make it possible to obtain objective attenuation information for the reasons of the ultrasound wave reflection properties as mentioned above. The Patents to Kossoff (U.S. Pat. No. 3,881,164) where author suggesting to improve focusing of A-mode transducer by using two transducers and Coleman et al. (U.S. Pat. No. 4,932,414) where author using mechanically moving A-mode transducer to make a scanning two-dimensional images to find out area of abnormality to apply radiation treatment are not belong to a two-frequency examination or attenuation measurement method and cannot be compared to Yukov Tissue Characterization Method. The Patent No. US20140350403 to KHO et al is a totally different method which applies multiple transducers focused in one point to evaluate the attenuation in that organ and it cannot be compared to Yukov Tissue Characterization Method.

Very sharp and short excitation pulses of a B-scan imaging system lead to a very high resolution of the tissue structure images. However, in many cases there is still not enough information to differentiate the type of abnormalities in the patient's body. B-scan imaging system need some extra information to resolve this problem. One type of needed information would account for different attenuation values according to the type of tissue.

The U.S. Pat. No. 5,361,767 to Yukov suggests using the Two-Frequency Method as a Tissue Characterization Method together with a B-scan tissue structure image information, which makes it easier to find a spot of interest for measurement of attenuation. This reference also suggests using the same B-scan transducer simultaneously, in sequence or alternately as a B-scan image visualization method and as a transducer for a Two-Frequency Attenuation Method in order to calculate attenuation data from a spot of interest for generating tissue characterization information. Yukov did not mention that there are fundamental differences between the requirements for B-scan transducers and Two-Frequency Attenuation Method transducers. B-scan transducers require different types of excitation pulses which must be very sharp and short to achieve high resolution of tissue structure images. In contrast, the excitation pulse for a Two-Frequency Method transducer consist of several sine-waves.

Another big difference is that a B-scan transducer requires multiple piezo-elements but a Two-Frequency Method transducer requires only one piezo-element (i.e., only one emitter-receiver source). Because of these differences there are limitations for applying a regular B-scan transducer for both methods. It is impossible to apply without re-design and re-engineering existing B-scan transducers to integrate two-dimensional visualization technique and A-mode transducer of Two-Frequency Attenuation Method technique as one combined transducer to have a high-quality ultrasound diagnostic examination.

Applying B-scan image visualization combined with a Two-Frequency Attenuation Method for tissue characterization can improve quality of the ultrasound diagnostic examinations and will make it possible to determine types of the tissue non-invasively in a living entity.

BRIEF SUMMARY OF THE INVENTION

It is an object of the present invention to improve the quality of current diagnostic examination methods by providing a YB-scan imaging system that can perform 2-dimensional ultrasound visualization at two frequencies with two-frequency attenuation analysis thereby allowing non-invasive determination of the type of tissue under investigation.

It is also an object of the present invention to improve the quality of current diagnostic examination methods by providing a system having a versatile transducer, which may be comprised of a combination of transducers, with the system further having components to permit generation of two-dimensional images, typically known as B-scan images, and with generation of two-frequency tissue characterization data, which may also be displayed graphically. According to the principles described herein, two-dimensional ultrasound images are used to identify a spot in a region of interest which is characterized by analysis of the two-frequency attenuation data.

One embodiment integrates, through a novel transducer, simultaneous application of a two-dimensional B-scan image visualization method and a two-frequency tissue characterization method where a B-scan image is used as a guiding image to be used with two-frequency tissue characterization data to overcome the aforementioned problems. B-scan images produced with this novel YB-scan transducer are referred to as YB-scan images or YB-images.

It is a further object of the present invention to improve the quality of ultrasound diagnostic examination with a system having a novel versatile transducer, fabricated from an existing B-scan transducer currently available on the market, or fabricated de novo, which can reversibly permit a subset of piezo-elements in the transducer to operate as an A-mode transducer. Additional system components would adapt conventional B-scan systems to perform both B-scan imaging and two-frequency A-mode tissue characterization using the novel versatile transducer, thereby enabling medical specialists to conveniently apply high resolution B-scan image information as a guiding image to use with two-frequency A-mode tissue characterization for accurate determination of tissue types when performing ultrasound imaging procedures. This system would employ a switching mechanism to switch the system between B-scan mode and tissue-characterization mode.

It is a further object of the present invention to improve the quality of ultrasound diagnostic examination with a system having a novel versatile combination transducer in which the transducer is fabricated from an existing B-scan transducer currently available on the market or fabricated de novo. The system is configured to be switched by an operator between B-mode imaging and A-mode tissue characterization. The combination transducer uses a conventional piezo-element array as a B-scan transducer and includes a separate piezo-element, which functions as an A-mode transducer, that is dedicated for two-frequency A-mode operation for tissue characterization. The combination transducer may have the A-mode piezo-element installed in a common housing with a B-scan piezo-element array or it may be contained within its own housing that is externally attached to the housing of a B-scan transducer. Alternatively, the B-mode transducer and A-mode transducer do not need to be physically attached to each other.

In accordance with one embodiment an operator uses the system by applying a YB-scan transducer receiving two-frequency excitation pulses for simultaneous generation of YB-scan tissue images and generation of two-frequency tissue characterization data and images. An operator places the YB-scan transducer on a patient's body; displaying YB-scan tissue images on a monitor; analyzes the YB-scan tissue images; selects a region of interest on said displayed YB-scan images on said monitor; displays A-mode signals on the screen next to the displayed said YB-scan images on said monitor; then the operator obtains objective attenuation data to determine the tissue type by automatically by having the system process the attenuation data or by visually analyzing he A-mode signals from the chosen region. The tissue characterization data may be displayed on the monitor next to the YB-scan image.

The embodiments using conventional B-mode scanning in combination with two-frequency A-mode tissue characterization require switching of the system between A-mode and B-mode operation. These embodiments involve performing B-scan imaging, selecting a region of interest followed by A-mode scanning of the spot of interest with two-frequency attenuation analysis for tissue characterization.

Details of the apparatus of present invention are set forth in the following detailed description and the accompanying drawings wherein like reference numerals depict like elements.

BRIEF DESCRIPTION OF THE SEVERAL VIEWS OF THE DRAWING(S)

Figure 4:
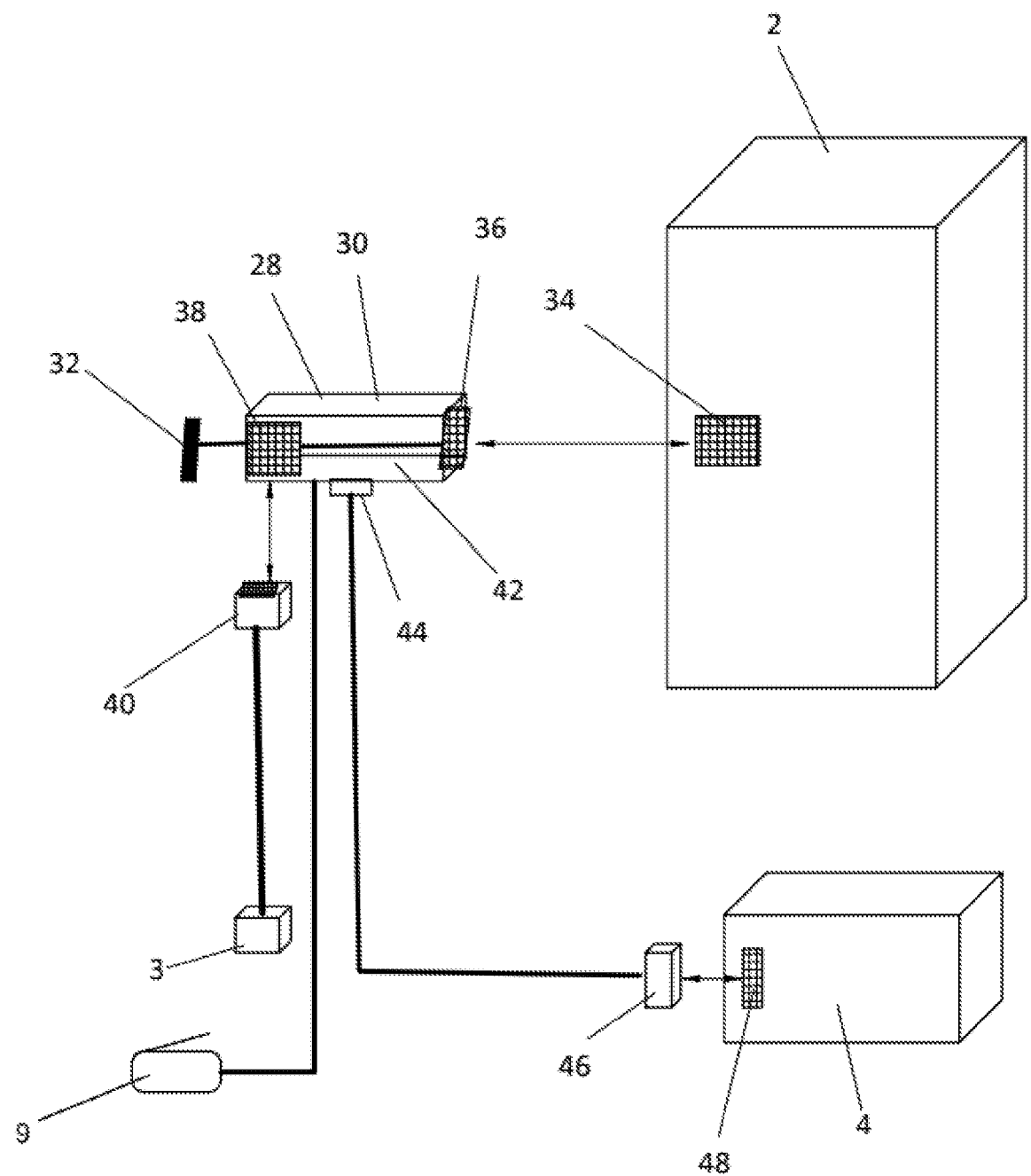

FIG. 4 schematically illustrates a system according to some embodiments of the invention wherein an adapter facilitates connections between a B-mode apparatus, a two-frequency apparatus, and a combined A-scan and B-scan transducer.

Figure 5:
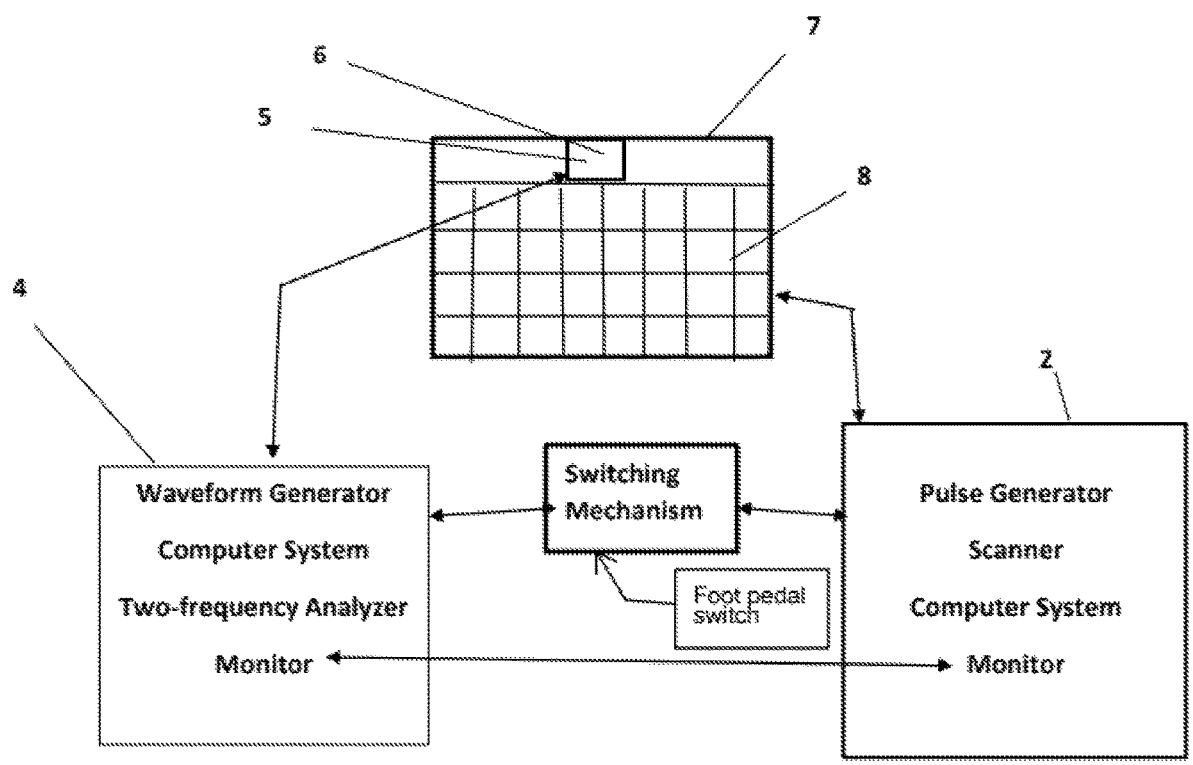

FIG. 5 is a schematic representation of a third embodiment of the invention which uses a switching mechanism to switch an ultrasound imaging system between conventional B-mode scanning and a two-frequency tissue characterization mode.

Figure 6:
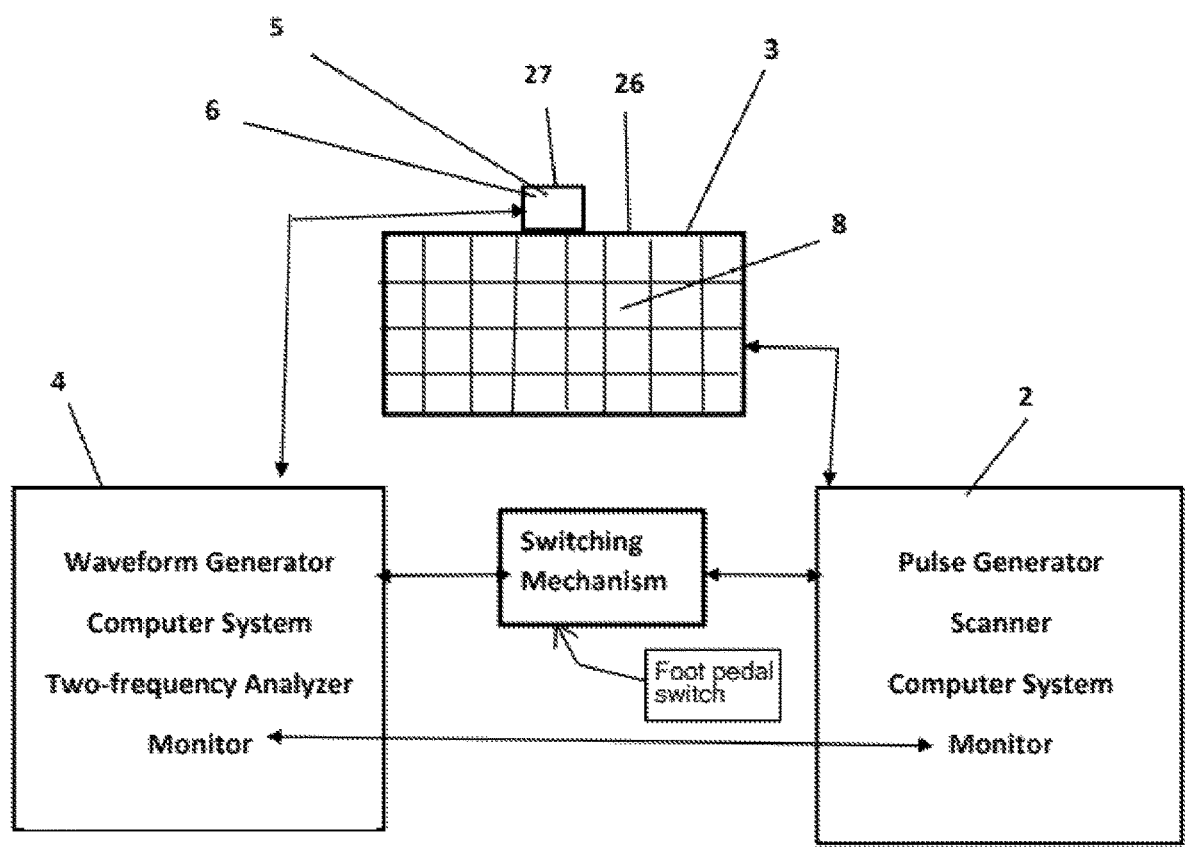

FIG. 6 is a schematic representation of a fourth embodiment of the invention which uses a switching mechanism to switch an ultrasound imaging system between conventional B-mode scanning and a two-frequency tissue characterization mode.

DETAILED DESCRIPTION OF THE INVENTION

Figure 1:
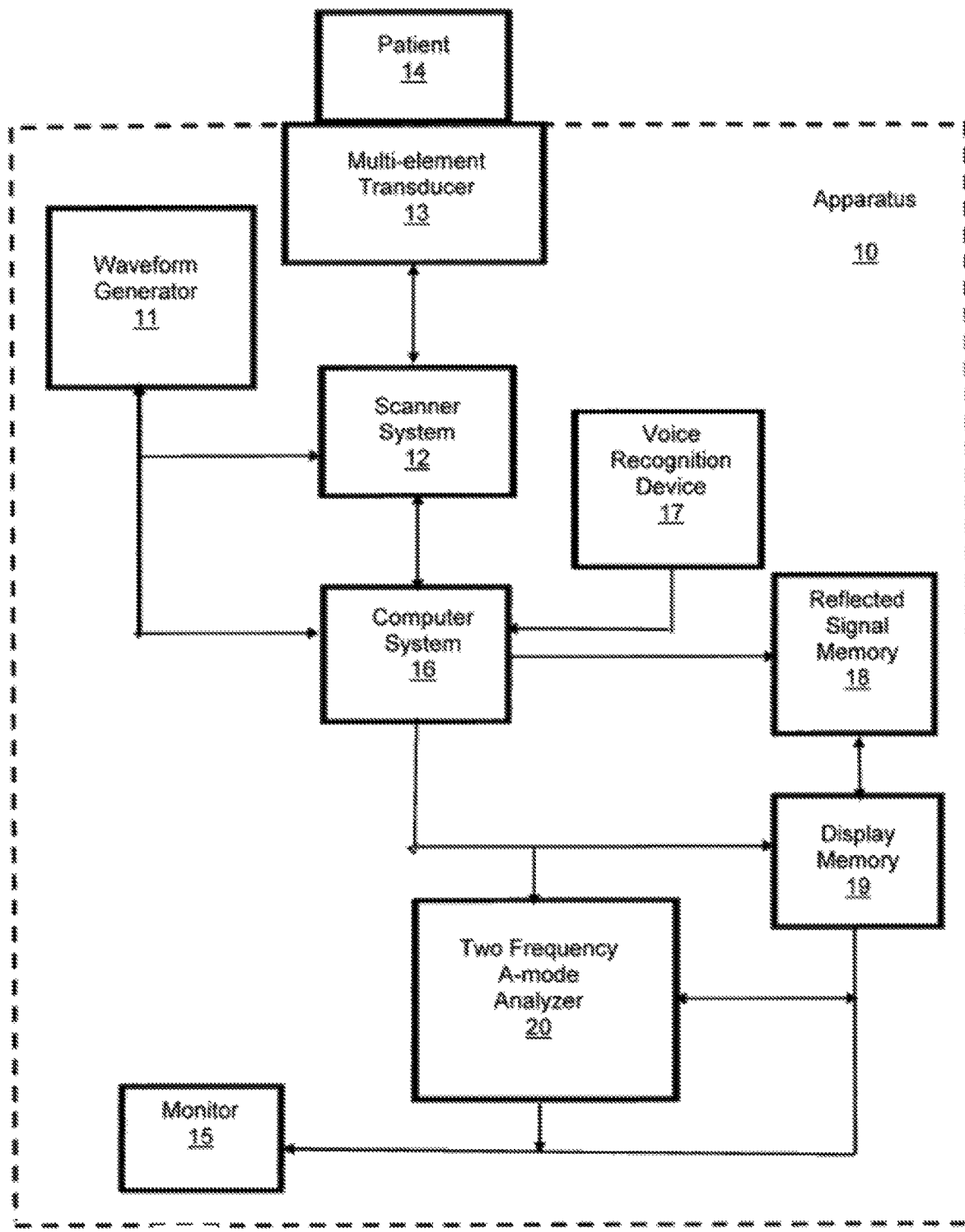
FIG. 1 is a schematic representation of an apparatus which can perform simultaneous application of the YB scan imaging and the tissue characterization method.

Referring now to the drawings, FIG. 1 illustrates an apparatus that is configured to function by simultaneously to producing 2-dimentional images (hereafter 'YB-scan images'), which are analogous to B-scan images, and also producing two-frequency characterization data. It may also produce a visual representation of the two-frequency characterization data. The apparatus 10 of FIG. 1 includes a plurality of piezo-elements which function as a multi-element transducer 13 (hereafter referred to as a 'YB-scan transducer'). In a preferred embodiment, all the piezo-elements may function separately and independently as an A-mode transducer. An arbitrary waveform generator 11 can generate pulses as desired at two different frequencies with desired width and shape. The apparatus 10 further includes a linear in a-sequence scanning system 12. The apparatus further includes a computer system 16 or controller. The computer system or controller further has memory 18 for storing reflected signals data, display memory 19, a two-frequency A-mode analyzer 20 and a monitor 15. The apparatus may also include a voice recognition device 17.

The excitation pulses from a waveform generator comprised of several sine-waves for each chosen frequency of two different frequencies are applied in sequence and the pulses separately excite each of the independently functioning piezo-elements of the YB-scan transducer. By connecting independently functioning piezo elements of a YB-scan transducer to a linear in-sequence scanning system a YB-scan image of a tissue is created with simultaneous application of A-mode signals thereby permitting calculation of attenuation data.

Each piezo- element of said YB-scan transducer 13 emits and receives signals on two different chosen frequencies having a specified width and shape from the waveform generator 11. An operator can place the multi piezo-elements YB-scan transducer 13 on the surface of the body of a patient 14 and display in a sequence two YB-scan images on two different frequencies for visualization on a monitor 15 by using computer system 16 with a program memory and control systems that are available on the market having all the features necessary for examination and analyzes of the YB-scan images so that the YB-scan images can be displayed in a sequence or individually by choice. On the screen of monitor 15 an operator can analyze any spot of interest on the YB-scan images by applying the tissue characterization method to determine the attenuation data for the spot of interest in the tissue under examination. Analysis of the A-mode signals from the chosen spot and calculation of the attenuation data from the chosen spot can be processed automatically and displayed as an overlay on the chosen spot on the screen displaying the YB-scan images. A living body consists of different types of tissues having layers and boundaries. A YB-scan imaging method displays the structure of the tissue layers and their boundaries. In many cases this information is not enough to differentiate the type of tissue. The tissue characterization apparatus can differentiate the type of tissue but only through reflected signals from boundaries of the layers because existing technology does not have enough accuracy to measure attenuation in the tiny structures of the tissue. The tissue characterization method requires two reflected signals to calculate the attenuation data between the reflected signals: one reflected signal from front boundary of the layer and a second reflected signal from the rear boundary of the layer. The YB-scan transducer 13 as described above consists of multiple piezo-elements which function independently for YB-scan imaging and for simultaneous tissue characterization according to the two-frequency method. The operator must know that each piezo-element has its own reflected image display. To measure attenuation in a spot of interest found through YB-scan image requires finding two reflected signals coming from the same piezo-element. The operator must click on a chosen reflected signal on the YB-scan image and a line will appear to show the direction of the reflected signals coming from the piezo-element. The operator must find and click on the second reflected signal from the same piezo-element and it should be a rear boundary of the chosen layer. The attenuation data will be displayed by choice on the YB-scan image screen as an overlaid color image or as numerical data between the chosen reflected signals or displayed as numerical data on a smaller screen next to the YB-scan image display on the monitor 15. If needed the operator can see and analyze the reflected signals from the corresponding piezo-element as A-mode signals which can be displayed on the screen of the monitor 15 next to the YB-scan image display. On the top of the YB-scan imaging screen of the monitor 15 there are numbers corresponding to each piezo-element of the YB-scan transducer 13. By clicking the number an operator can activate the direction line of the piezo-element. The operator also can use a Voice Recognition block 17 to activate the direction line of any piezo-element by pronouncing a number to find a corresponding piezo-element. The operator also can use A-mode Analyzer block 20 to make analyses of said A-mode signals automatically. The display of YB-scan tissue images simultaneously with overlaid tissue characterization information will greatly improve the quality of ultrasound diagnostic examinations.

In accordance with the present invention the combined method of B-scan imaging with the two-frequency tissue characterization can also be accomplished by using a high-resolution B-scan system having a B-scan transducer with an array of piezo-elements.

Figure 2:
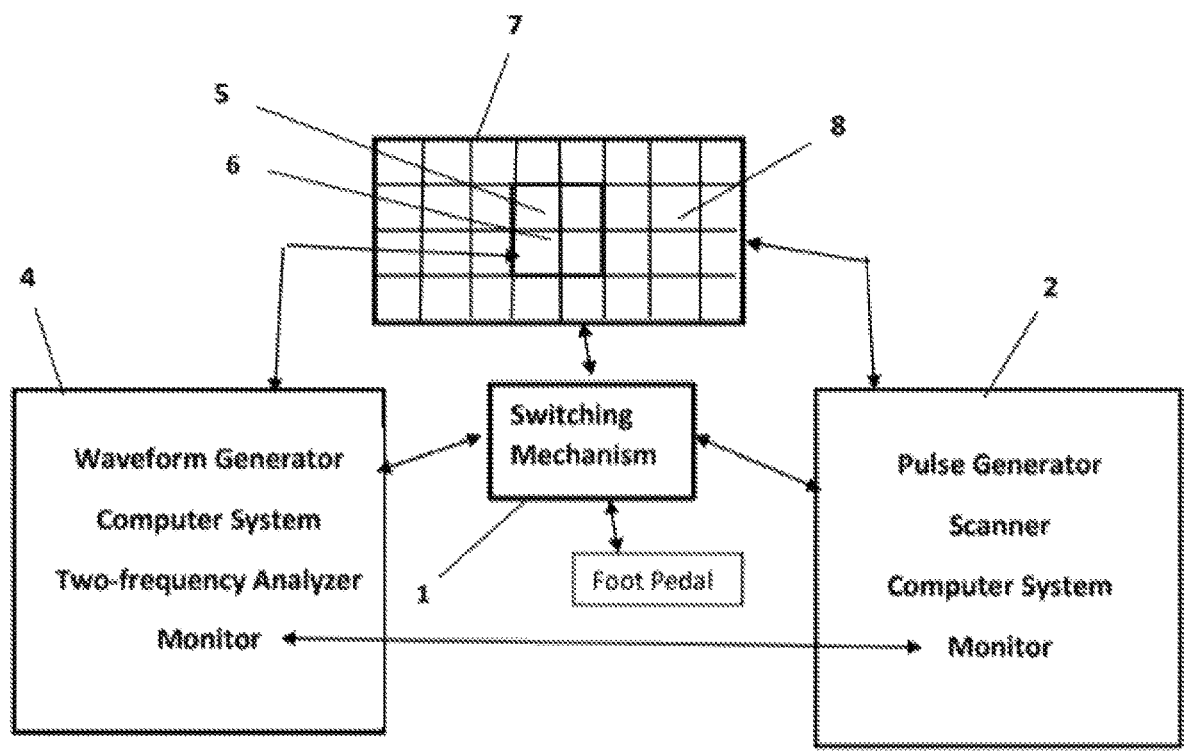
FIG. 2 is a schematic representation of a second embodiment which uses a switching mechanism to switch an ultrasound imaging system between conventional B-mode scanning and a two-frequency tissue characterization mode.

The embodiment of FIG. 2 has a combined transducer which can receive two different types of excitation pulses for performing high-resolution B-scan imaging and two-frequency attenuation analysis for tissue characterization. The two-frequency attenuation method requires one emitting and receiving source of ultrasound signals. An operator performing the tissue characterization method determines the tissue type from analysis of the registered reflected signals from the tissue. For medical specialists it is very important to know from what part of the region of interest the attenuation data is coming from. The same problem was encountered with needle biopsy examination procedures. Later specialists invented x-ray and ultrasound guiding images for needle biopsy procedures. The same problem exists with applying tissue characterization examination. It needs two-dimensional image information to direct an A-mode transducer to a chosen spot in a region of interest. A B-scan transducer has a plurality of tiny piezo-elements and requires very short excitation pulses. A-mode transducers require sinusoidal excitation pulses using two different frequencies. The A-mode transducer must be much larger than a single conventional B-mode piezo-element to emit a signal with sufficient strength to generate reflected signals suitable for two-frequency attenuation analysis. The A-mode transducer requires independent functioning piezo-elements in both emitting and receiving modes but the B-scan transducer's piezo-elements are not independent functioning. For these reasons an A-mode transducer can be integrated with a B-scan transducer by redesigning the function of some part of its piezo-elements to connect them together through a switching system to function as A-mode transducer and to connect with the waveform generator of tissue characterization apparatus for sinusoidal excitation pulses on two different frequencies. The designed A-mode transducer becomes independent functioning for the period of tissue characterization examination. The middle part of B-scan transducer is the best place to design A-mode transducer. The A-mode transducer may be comprised of a row of the piezo-elements. The required number of tiny piezo-elements that should be connected together to make an A-mode transducer will depend on the applied frequencies used and the depth of region of interest. Electronic switch mechanism should consider different options of number of the tiny piezo-elements to be connected together to function as an A-mode transducer for the operator to apply. There is another switching function in this embodiment which should turn ON the functioning apparatus and turn OFF another one with switching at a controllable speed because the best of examination can be when the operator visualizes both images on the screen of monitor almost simultaneously. This embodiment has a combined transducer that uses an A-mode transducer inside of a B-scan transducer. The combined transducer can be fabricated from a pre-existing conventional multi-piezo-element B-scan transducer. The A-mode transducer is comprised of a subset or group of piezo-elements of the pre-existing B-scan transducer.

A B-scan transducer is positioned in a housing 7, the B-scan transducer is comprised of a plurality of piezo-elements 8 in an array. A switching mechanism 1 is configured to reversibly connect a group of adjacent piezo-elements 5 from the plurality of piezo-elements such that the group of piezo-elements together function as an A-mode transducer 6. A foot pedal switch 9 is used by an operator to reversibly activate switching mechanism 1 to actuate A-mode transducer function. When A-mode function is actuated the switching mechanism electronically communicates with both the two-frequency apparatus and the group of piezo-elements functioning in A-mode within the transducer housing. When A-mode function is not activated, the switching mechanism electronically communicates with the B-mode apparatus 2. It is evident to a person of ordinary skill in the art that the arrangement of the group of adjacent piezo-elements 5 can be a row of piezo elements or another suitable configuration.

The foot pedal effectively toggles the system between said B-scan mode and two-frequency tissue characterization A-scan mode thereby enabling both B-scan imaging and tissue characterization imaging.

By using a B-scan image as a guiding image, an operator can select a region of interest to be scanned in two-frequency A-mode for tissue characterization thereby improving the quality of existing ultrasound diagnostic examination methods.

Figure 3:
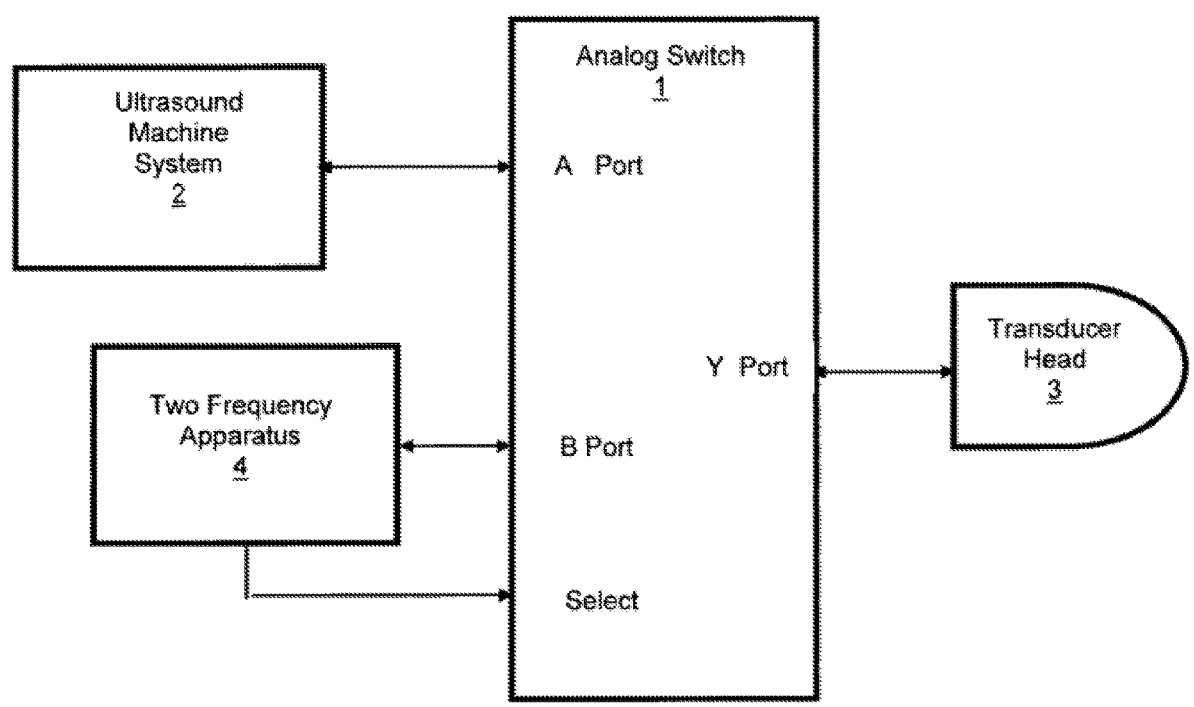
FIG. 3 is a schematic representation of a switching mechanism which enables an ultrasound imaging system according to the principles of the invention to switchably operate in either a two-frequency A-scan mode or a conventional B-scan mode.

In accordance with the present invention any currently marketed B-scan apparatus with B-scan transducer having a plurality of piezo-elements can be adapted for combining conventional B-scan examination and two-frequency tissue characterization essentially by employing a switching mechanism such as shown in FIG. 3. The switching mechanism can be integrated into the system through an interface adapter as shown in FIG. 4, thereby allowing the system to function for B-scan imaging and two-frequency tissue characterization imaging. By combining B-scan imaging and two-frequency tissue characterization improved quality of existing ultrasound diagnostic examination can be achieved.

FIG. 3 is a block diagram of an electronic switching mechanism which can connect together some of the piezo-elements of a B-scan transducer to make a connected adjacent group of piezo-elements to function as an A-mode transducer as describe above (see FIG. 2) for two-frequency tissue characterization.

Electronic switching mechanism (FIG. 3) works through a TTL logic level signal via Analog Switch 1. When it is driven with a logic "1" the System 2 of the ultrasound apparatus is connected to the transducer Head 3. Also, it is "pulled up", when nothing is connected to the input, the ultrasound apparatus System 2 is connected to the transducer Head 3. When it is driven with a logic "0" (or shorted to ground) all elements are disconnected from the ultrasound apparatus System 2 and the "IN" signal from tissue characterization apparatus 4 through B-port of said Analog Switch 1 is connected to the central elements of the transducer Head 3. A high voltage switch IC can be used for a relay which provides switching of the group of piezo-elements 5 between the B-scan apparatus 2 and the Tissue Characterization apparatus 4. The remaining number of piezo-elements have a single switch for each piezo-element so that all piezo-elements of the B-scan transducer see the same impedance when driven by the B-scan apparatus. These switches are opened by disconnecting the B-scan apparatus's system from the transducer when the external transceiver is connected to the group of piezo-elements 5.

The electronic switching mechanism of FIGS. 2 & 3 can be installed within the interface adapter shown schematically in FIG. 4. The interface adapter is constructed with a space 42 to accommodate the switching mechanism. The interface adapter connects the B-scan transducer 7 (FIG. 2) with the B-scan apparatus 2 through the switching mechanism described above.

An interface adapter housing 30 holds two types of connectors. A connector 36 on the front side of the interface adapter is configured to connect with the B-scan apparatus at connector 34. Another connector 38 on the lateral side of interface adapter allows for connection of the B-scan transducer to the interface adapter by connecting connector 40 with connector 38. The interface adapter is also connected to the two-frequency apparatus. The interface adapter can be locked or unlocked using a rod with handle 32.

In another aspect of the present invention existing ultrasound diagnostic examination can be improved by combined application of a B-scan imaging method and A-mode two-frequency tissue characterization with a conventional multi piezo-element B-scan transducer having a single piezo-element inserted within the housing of the B-scan transducer. Unlike the embodiment of FIG. 2, which utilizes a subset or group conventional tiny B-mode piezo-elements to reversibly form an A-mode transducer, the embodiments of FIGS. 5 and 6 utilize a single large A-mode piezo-element as the A-mode transducer.

FIG. 5 is a schematic illustration of a combined transducer which integrates a B-scan transducer having an array of piezo-elements 8 with an inserted A-mode transducer 6 within housing 7. The B-scan transducer is comprised of plurality tiny piezo-elements for B-mode scanning and the A-mode transducer 6 is comprised of a single piezo-element 5—which is larger than the tiny B-mode piezo-elements. The A-mode transducer is connected directly to the tissue characterization apparatus 4. The A-mode transducer 6 functions separately and independently from the piezo-element array 8 of the B-scan transducer. The size of the A-mode transducer piezo-element depends on the values of the applied two frequencies and the depth of a region of interest to be characterized in the patient's body and also depends on the particular organ under investigation. The combined examination starts with B-scan visualization process whereby an operator finds a spot or region of interest. The operator then depresses a foot pedal or other convenient mechanical means to switch from B-mode to A-mode scanning and slides the combined transducer to position the A-mode transducer for examining the spot or region of interest. An advantage of this embodiment in comparison to the embodiment of FIG. 2 is that the switching mechanism does not need to be connected directly to the piezo-elements of the combined transducer. This is because the dedicated A-mode piezo-element does not need to be electronically connected to a group dual-function piezo-elements. The single piezo-element transducer can also function as a focused transducer when needed.

Reflected signals are analyzed by shape, width and registered time visually or automatically through two-frequency analyzer block to obtain attenuation data for the chosen spot of interest thereby permitting determination of the type of tissue under investigation.

Another embodiment using a single A-mode piezo-element for tissue characterization in combination with a B-mode transducer is shown in FIG. 6. Any commercially available B-scan apparatus with any type of B-scan transducer can be adapted for combined B-scan imaging and A-mode two-frequency tissue characterization according to this embodiment which is similar to the embodiment of FIG. 5, having an A-mode transducer 6 comprised of a single piezo-element 5, but the single A-mode piezo-element in the embodiment of FIG. 6 is positioned within its own housing 27 which is in turn affixed to the B-mode transducer housing 26. This embodiment is essentially the same as the embodiment of FIG. 5 except that the A-mode transducer is external to the B-scan transducer housing.

During the examination of the patients by placing the bodies of said B-scan transducer and said A-mode transducer adjacent to each other as one combined transducer and to use B-scan visualization as a guiding image information to apply tissue characterization method. The examination process of the patients is the same as practiced for the embodiment of FIG. 5. Any existing B-scan apparatus on the market can be configured with adjacent B-scan and A-mode transducers according to this embodiment.

It is apparent that there has been provided in accordance with this invention devices and methods for non-invasively determining a type of tissue within a living entity which fully satisfies the objects, means and advantages set forth herein. While the invention has been described in combination with specific embodiments thereof, it is evident that many alternatives, modifications and variations will be apparent to those skilled in the art in light of the foregoing description. Accordingly, it intended to embrace all such alternatives, modifications and variations as fall within the spirit and broad scope of the appended claims

I claim:

1. An ultrasound imaging system to be used by an operator comprising:
   a YB scan transducer (13) having a plurality of piezo elements wherein each of the piezo elements are configured to function separately and independently as A-mode transducers, said piezo-elements configured to be excited in sequence at two different frequencies, wherein said two different frequencies are applied in sinusoidal two-pulse sequences, said piezo-elements further configured to receive reflected signals at said two different frequencies which are applied in said two-pulse sequences,
   a waveform generator, said waveform generator configured to produce the two sinusoidal impulses on two different frequencies in said two-pulse sequences, a scanner system, a computer system or controller, said computer system or controller having memory for storing reflected signals data and memory for display, a two-frequency A-mode analyzer, a monitor,
   a linear in-sequence scanning system, said transducer connected to said linear in-sequence scanning system,
   said waveform generator in electronic communication with said scanner system and said computer system or controller, said scanner system also in electronic communication with said computer system or controller,
   said system further configured to generate at least one two-dimensional YB-scan images corresponding to said two different frequencies applied in sequence,
   said system further configured wherein said two-frequency A-mode analyzer receives reflected signal data from tissue layers and further wherein said two-frequency A-mode analyzer finds or permits the operator to find a pair or pairs of reflected signals of said two different frequencies, said pair of reflected signals deriving from the same single piezo-element or said pairs of reflected signals each deriving from a respective single piezo element,
   said two-frequency A-mode analyzer configured to analyze said reflected signals on said two different frequencies to determine frequency, shape, width and registered time of said reflected signals, and sends selected reflected signals on said two different frequencies to the computer to calculate a differential attenuation coefficient for the tissues under investigation, thereby generating two-frequency attenuation information,
   said system further configured to display said at least one two-dimensional YB-scan image from wherein said YB-scan image may be combined with said two-frequency attenuation information in an enhanced image or be displayed separately as required by the operator, thereby permitting differentiation between types of tissue within an organ.

2. The ultrasound imaging system of claim 1 further comprising, wherein
said plurality of piezo elements is comprised of a row of piezo-elements.

3. The ultrasound imaging system of claim 1 further comprising, wherein said waveform generator is configured to produce two types of excitation pulses in a sequence or alternating, said two types comprising said two sinusoidal pulses in said two-pulse sequence, said two-pulse sequence comprising pulses of two different frequencies, and a second type or pulses having greater amplitude and shorter duration than said two sinusoidal pulses in said two-pulse sequence.

4. The ultrasound imaging system of claim 1 further comprising wherein said imaging system is configured to display said two-frequency A-mode information as a two-frequency attenuation image.

5. The ultrasound imaging system of claim 3 further comprising wherein said imaging system is configured to display said two-frequency A-mode information as a two-frequency attenuation image.

6. A method for non-invasively determining at least one of a type of a tissue matter and a state of said tissue matter in a living body using an apparatus, said method comprising the steps of:
providing said apparatus having a YB scan transducer (13), said YB scan transducer comprising a plurality of separately and independently functioning piezo-elements, said transducer configured to be placed on said tissue matter, said apparatus further having a waveform generator for generating sinusoidal pulses at two different frequencies, said apparatus yet further having a linear in-sequence scanning system, reflected signal memory, and a two-frequency analyzer,
said waveform generator generating said pulses at said two different frequencies,
supplying said pulses at said two different frequencies to said transducer,
directing said pulses at said two different frequencies to a tissue,
receiving reflected signals data,
storing reflected signal data at said two different frequencies in said reflected signal memory,
storing digital two-dimensional image data in display memory,
generating two-dimensional YB-scan images at said two different frequencies,
displaying at least one two-dimensional YB-scan image on a monitor,
choosing a spot in a region of interest on said at least one two-dimensional YB-scan image,
determining received reflected signals registered from a same piezo-element,
displaying A-mode images on said monitor, said A-mode images generated from said reflected signal data on said two different frequencies, wherein said A-mode images are displayed along with said at least one two-dimensional image,
analyzing A-mode reflected signals from the spot in said region of interest to determine frequency, shape, width and registered time of said A-mode reflected signals,
creating a two-frequency attenuation image of said spot in said region of interest on said monitor,
determining a type of tissue matter and the state of the tissue matter.

* * * * *